United States Patent [19]
Maas et al.

[11] Patent Number: 4,761,372
[45] Date of Patent: Aug. 2, 1988

[54] **MUTANT ENTEROTOXIN OF *E. COLI***

[75] Inventors: Werner K. Maas, Hastings-on-Hudson, N.Y.; Carlton L. Gyles, Guelph, Canada

[73] Assignee: New York University, New York, N.Y.

[21] Appl. No.: 683,701

[22] Filed: Dec. 19, 1984

Related U.S. Application Data

[63] Continuation-in-part of Ser. No. 224,046, Jan. 12, 1981, abandoned.

[51] Int. Cl.$^4$ .................... C12M 15/00; C12P 19/32; A61K 39/02; A01N 63/00
[52] U.S. Cl. ................................. 435/172.1; 435/91; 435/253; 435/849; 424/92; 424/93; 935/22; 935/27; 935/56; 935/63; 935/64; 935/65
[58] Field of Search ................... 435/172.1, 317, 253, 435/91, 849; 424/92, 93; 935/22, 27, 56, 63, 64, 65

[56] References Cited

PUBLICATIONS

Johnson, D. A. et al., Journ. of Bact., 143 No. 3:1171–1178, (1980).
Myron M. Levine et al., Microbiological Reviews, vol. 47, pp. 510–550 (1983).
Tien-Mi Chen, Infection and Immunity, vol. 47, pp. 5–10 (1985).
Randall K. Holmes, "Genetic Aspects of Toxinogenesis in Bacteria", reprinted from *Microbiology*, pp. 296–301 (1975).
Randall K. Holmes, "Studies on Toxinogenesis in *Vibrio cholerae* III. Characterization of Nontoxinogenic Mutants in Vitro and Experimental Animals", reprinted from *The Journal of Clinical Investigation*, vol. 55, No. 3, (Mar. 1975).
James Kaper et al., "Recombinant Nontoxinogenic *Vibrio cholerae* Strains as Attenuated Cholera Vaccine Candidates", *Nature*, vol. 38, pp. 655–658 (1984).
Gyles, C. L. et al., *J. Infect. Dis.* 130, 40 (1974).
Gyles, C. L. et al., *Science* 198 198 (1977).
Silva, M. L. M. et al., *Proc. Natl. Acad. Sci. USA* 75, 1384 (1978).
So, M. et al., *J. Bacteriol.* 128, 463 (1976).
So, M. et al., *Infec. Immun.* 21, 405 (1978).
Adelberg, E. A. et al., Biochem. Biophys. Res. Comm. 18, 788 (1965).
Bramucci, M. G. & Holmes, R. K., J. Clin. Microbio. 8, 252 (1978).
Broda, P., Plasmids, W. H. Freeman & Co., San Francisco, pp. 120–122, 83–99, 43–46 (1979).
Dallas, W. S. & Falkow, S., Nature 277, 406 (1979).
Donta, S. T. et al., Science 183,334 (1974).
Dubnau, E. & Maas, W. K., *J. Bacteriol.* 95, 531 (1968).
Goebel, W. et al., *Molec. Gen. Genet.* 157, 119 (1977).
Gyles, C. L. & Barnum, D. A., *J. Infect. Dis.* 120, 419 (1969).
Honda, T. & Finkelstein, R. A., *Proc. Natl. Acad. Sci. USA* 76, p. 2052 (1979).
Koyama, A. H. et al., *J. Bacteriol.* 122, 73 (1975).
Pfister, A. et al., *J. Bacteriol.* 127, 348 (1976).
Reis et al., *Infec. Immun.* 29, 140 (1980).
Sack, D. A. & Sack, R. B., *Infect. Immun.* 11, 334 (1975).
Sack, R. B., *Ann. Rev. Microbiol.* 29, 333 (1975).
Sack, R. B. et al., *J. Infect. Dis.* 123, 378 (1971).
Smith, H. W. & Parsell, Z., *J. Gen. Microbiol.* 87 129 (1975).

*Primary Examiner*—Robert J. Warden
*Assistant Examiner*—Jack Spiegel
*Attorney, Agent, or Firm*—Spencer & Frank

[57] ABSTRACT

A plasmid which comprises genes coding for an immunogenic, non-toxic, heat-labile enterotoxin and/or a non-toxic, heat-stable enterotoxin are disclosed. The *E. coli* containing this plasmid is also described. The *E. coli* or the plasmids may additionally contain a colonization factor. Methods for producing the plasmid and the *E. coli* containing the same are described. A live vaccine is prepared with the *E. coli* and is useful for vaccinating humans and animals against certain diarrheal diseases.

24 Claims, 4 Drawing Sheets

MUTANT ENTEROTOXIN OF E. COLI

CROSS REFERENCE TO RELATED APPLICATION

This application is a continuation-in-part of our application Ser. No. 224,046 filed Jan. 12, 1981, now abandoned, the entire specification of which is incorporated herein by reference.

BACKGROUND OF THE INVENTION

The bacterial-mediated diarrheal diseases include cholera, typhoid fever, traveler's diarrhea and acute diarrheal illness in infants. The diseases are basically of two types, invasive and non-invasive gastroenteritis. Typhoid fever is representative of the invasive type which is characterized by invasion of the intestinal mucosa by the pathogen. In the non-invasive type, the symptoms are effected by a bacterial toxin which stimulates an enormous increase in the secretory activity of the cell lining the small intestine causing an acute loss of body fluid.

In the last decade, *E. coli* has been shown to be the agent responsible for a large portion of previously undiagnosed diarrheal disorders. It has also been determined that *E. coli*-mediated diarrheal diseases affect not only humans but also agricultural animals, especially cattle and hogs. The newborn of the species is particularly susceptible, and the agricultural industry suffers sizable loss of livestock each year from outbreaks of these diseases.

The *E. coli*-mediated diarrheal diseases are of the non-invasive type, effected by one or more toxins (or entrotoxins) made by pathogenic strains of *E. coli*. Two types of toxin, classified as heat-labile (hereinafter LT) and heat-stable (hereinafter ST) have been found in pathogenic *E. coli* strains causing diarrheal diseases in humans and animals (Sack, R. B., *Ann. Rev. Microbiol.*, 29, 333 (1975)). The genes controlling the production of these toxins are located on plasmids (Gyles, C., et al, *J. Infect. Dis.*, 130, 40 (1974)). In particular, a plasmid designated pCG86 has been isolated and extensively characterized. Plasmid pCG86 is a naturally-occurring recombinant plasmid which contains the genes for LT and ST and several genes for drug resistance. LT is antigenic and partially cross-reactive with anti-cholera antibodies while ST is poorly antigenic. LT is a high molecular weight protein composed of two types of subunits, one (B) having a molecular weight of 11,000 and the other (A) a molecular weight of 25,000 (Dallas, W. S. and Falkow, S., *Nature*, 277, 406 (1979)). ST has a molecular weight of less than 10,000. Two different types of ST have been discovered, e.g., one ST is active in infant mice, whereas the other is not.

Plasmids have been isolated from pathogenic *E. coli* carrying drug resistance genes and genes for producing the toxins. (So, M., et al, *J. Bacteriol.*, 128, 463 (1976) and Gyles, C. L., et al, *Science*, 198, 198 (1977). Such plasmids are naturally-occurring recombinant plasmids. The gene coding for LT has been cloned in a multicopy plasmid (So, M., et al, *Infec. Immun.*, 21, 405 (1978)). Variants of pCG86 have been produced bearing mutations in the LT gene or the ST gener. (Silva, M. L. M., et al, *Proc. Nat. Acad. Sci. USA*, 75, 1384 (1978)). Loss of LT toxicity can result from mutation in either the A or B subunit. The presence of a plasmid containing the genes for LT, ST or both has been shown to be insufficient for causing diarrheal disease. A colonization factor, a specialized adherence pili, which is antigenic, is also required. This colonization factor is required for the pathogenic *E. coli* to adhere and proliferate in the small intestine. The colonization factor gene may be carried on the same or a separate plasmid. For a review of this material, see Broda, P., *Plasmids*, W. H. Freeman & Co., San Francisco, Ca., pp. 120-122 (1979).

Although the toxins exert their effect in the lumen of the gut and do not enter the bloodstream, it is possible to provide immunity of the IgA type against antigenic proteins produced by resident bacterial strains. Thus, for example, recovered cholera patients are immune to further challenges, and they have been shown to have protective antibodies in their gastrointestinal tracts. Immunity can be generated by promoting antibody formation against the enterotoxins or against the colonization pili. For a review, see Levine, M. M., et al, *Microbiol. Rev.* 47, 510 (1983). Immunity can be provided by administering a live vaccine in the form of a mutant bacterial strain producing an altered toxin, lacking toxic effects but able to elicit antibodies capable of cross reacting with and inactivating the wild-type toxin. The foregoing approach has been applied successfully in the case of cholera, which produces an antigenic toxin (Honda, T. and Finkelstein, R. A., *Proc. Nat. Acad. Sci. USA*, 76, 2052 (1979)). Prior to the present invention, it was not possible to apply this technique to achieve immune protection against pathogenic *E. coli* because of the toxicity of both LT and ST and the requirement of an additional colonization factor. The present invention provides a strain of *E. coli* capable of colonization which produces an immunogenic LT lacking toxicity and a non-toxic ST. As used herein, a gene (or strain) producing a non-toxic ST refers to a gene (or strain containing such gene) which either produces a mutant ST that is non-toxic or does not produce any ST at all. The immunogenic LT is capable of eliciting a protective IgA response when produced by the strain of *E. coli* which is now nonpathogenic. The present invention also provides a recombinant plasmid, containing genes coding for an immunogenic, non-toxic LT capable of eliciting an antibody which neutralizes naturally occurring toxins.

SUMMARY OF THE INVENTION

The present invention discloses plasmids which contain genes coding for an immunogenic, heat-labile toxin (LT) which lacks toxicity and a non-toxic, heat-stable toxin (ST). The invention further describes strains of *E. coli* containing these plasmids. Either the *E. coli* or the plasmids can additionally contain a gene coding for a colonization factor which enables the bacteria to adhere and grow in the small intestine. Methods for producing the plasmids and strains of *E. coli* are also described.

A live vaccine comprising *E. coli*, having a colonization factor and the above-described plasmids are disclosed. This vaccine is useful for immunizing humans and animals against pathogenic *E. coli*-caused diarrheal diseases.

DETAILED DESCRIPTION OF THE INVENTION

Figure 1:
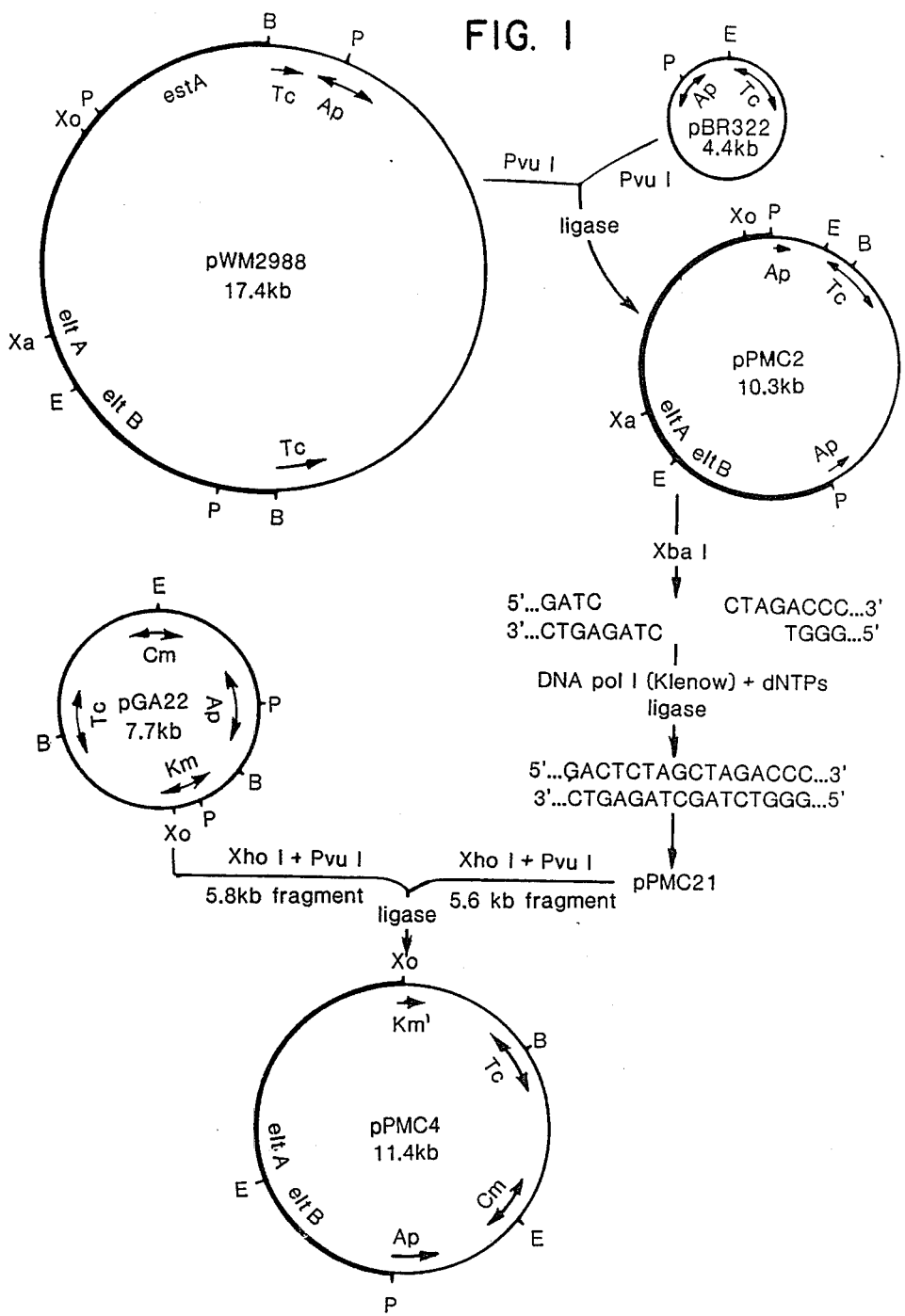
FIG. 1 illustrates the construction of plasmid pPMC4, wherein the following abbreviations apply: B, BamHI; E, EcoRI; P, PvuI; Xa, XbaI; Xo, XhoI; Ap, Cm, Km, Tc, resistance to ampicillin, chloramphenicol, kanamycin, and tetracycline, respectively; elt, heat-labile enterotoxin; estA, heat-stable enterotoxin.

The present invention utilizes conventional techniques of molecular genetics. For a review of the elements of molecular genetics, such as recombination, bacterial conjugation, transformation and transduction, see Stanier, R. Y., Doudoroff, M. and Adelberg, E. A., *The Microbial World*, 3rd Ed., Prentice-Hall, Inc., Englewood Cliffs, New Jersey, pp. 380–522 (1970); Strickberger, M. W., *Genetics*, The Macmillan Company, New York, N.Y., pp. 385–418 (1968); and Broda, P., supra, pp. 83–99. In the description which follows, standard genetic nomenclature is used. For example, $LT^+$ refers to a gene producing a normal, toxic LT; $LT^{31}$ refers to a mutant gene which produces a non-toxic LT; $Tc^R$ refers to a gene providing for resistance to tetracycline; and $Tc^S$ refers to tetracycline sensitivity caused by loss or mutation of the gene providing tetracycline resistance. In addition, the abbreviation CRM for immunologically cross-reacting material is used. Thus, $LT^-CRM^+$ refers to a mutant gene which products a mutant LT that is not toxic but cross-reacts with an antibody against normal LT, i.e., an immunologically active, non-toxic LT. $ST^-$ refers to a mutant gene which either produces a mutant ST that is not toxic or does not produce any ST at all.

According to one embodiment of the present invention, a plasmid is produced which contains genes coding for $LT^-CRM^+$ and $ST^-$. One method for preparing an $LT^-CRM^+ST^-$ plasmid is to utilize an $LT^+ST^-$ plasmid (in *E. coli* K12) as the starting plasmid. A $ST^-$ mutant of pCG86 is prepared by mutagenesis and penicillin enrichment followed by another round of mutagenesis, as described by Silva, M. L. M., et al, supra. Plasmid pCG86 is $LT^+ST^+$, $Tc^R$, $Sm^R$, $Su^R$, $Tra^+$ (Sm=Streptomycin, Su=sulfonamides and Tra=conjugal transfer). The $ST^-$ mutant of pCG86 is identical to the parent plasmid except for the ST gene. The $ST^-$ mutant is isolated and subjected to mutagenesis by N-methyl-N'-nitro-N-nitrosoguanidine (Ngd) treatment and selection for $ST^-$, $Tc^S$ mutants by penicillin enrichment in the presence of tetracycline, as described by Silva, M. L. M., et al, supra, and Koyama, A. H., et al, *J. Bacteriol.*, 122, 73 (1975). $Tc^S$ mutants do not grow in the presence of tetracycline and are therefore spared the lethal effects of penicillin. The $ST^-$, $Tc^S$ mutant is again subjected to mutagenesis using Ngd as described by Silva, M. L. M, et al, supra, and Adelberg, E. A., et al, *Biochem. Biophys. Res. Comm.*, 18, 788 (1965), this time selecting for $Tc^R$ revertants. A high proporation of such revertants are also $LT^-$. The $LT^-$, $ST^-$, $Tc^R$ mutant is verified to be $LT^-$ by performing an assay for LT as described by Donta, S. T., et al, *Science*, 183, 334 (1974) and Sack, D. A. and Sack, B. R., *Infact. Immun.*, 111, 334 (1975). This mutant is further examined to determine if CRM is produced utilizing the procedure described by Bramucci, M. G. and Holmes, R. K., *J. Clin. Microbiol.*, 8, 252 (1978) or by a radioimmunoassay using an antibody to cholera toxin. The mutants which are $LT^-CRM^+$, $ST^-$, $Tc^R$ are then isolated.

A second method for producing an $LT^-CRM^+$, $ST^-$ plasmid is to utilize an $LT^-$ plasmid as one of the starting materials. This plasmid is prepared as described by Silva, M. L. M., et al., supra and examined for production of CRM as described by Bramucci and Holmes, supra. An $LT^+$, $ST^-$ plasmid is prepared by insertion of transposon 5 (Tn5) carrying the gene for Kanamycin (Kn) resistance into the ST gene. (For a brief review of transposons, see Broda, P., supra, pp. 43–46). This is done by transducing cells containing pCG86 ($LT^+$, $ST^+$) with lambda (λ) phage containing Tn5 using conventional transduction techniques. Tn5 can insert either in the chromosomal DNA or plasmid DNA. Insertions in the plasmid are isolated by first selecting for $Kn^R$ and then by selecting for the ability to transfer $Kn^R$ to $F^-$ bacteria (bacteria which act as recipients of plasmids). It was discovered that a proportion of bacteria having Tn5 inserted in the plasmid are of the $LT^+$, $ST^-$, $Kn^R$ phenotype. Bacteria containing this plasmid are grown and infected with P1 phage as described by Pfister, A., et al. *J. Bacteriol.*, 127, 348 (1976). This results in encapsulation of the $LT^+$, $ST^-$, $Kn^R$ plasmid in the P1 phage. Bacteria which are $Kn^S$ and have the $LT^-CRM^+$, $ST^+$ plasmid are then transduced as described by Pfister, A., et al, supra. The $LT^-$, $ST^-$ transductants are then examined to determine if CRM is produced as described by Bramucci and Holmes, supra. The strains which contain an $LT^-$ $CRM^+$, $ST^-$ plasmid are then isolated.

A third method is to utilize a hyperproducing $LT^+$, $ST^+$ strain as the starting material. The hyperproducing $LT^+$, $ST^+$ strain is prepared by transposition of transposon 3 (Tn3) carrying the gene for ampicillin (Ap) resistance. This is accomplished by mating bacteria containing plasmid Rsc 13 (containing Tn3) with bacteria containing pCG86, as described by Goebel, W., et al, *Molec. Gen. Genet.*, 157, 119 (1977), and selecting for ability to transfer $Ap^R$ to an $F^-$ strain. Unexpectedly, insertion of Tn3 into pCG86 resulted in hyperproduction of LT in 20%–50% of $Ap^R$ isolates. LT hyperproducers are identified using the assay procedure of Bramucci and Holmes, supra, and then isolated. A hyperproducing $LT^-$ $CRM^+$, $ST^-$ plasmid is then prepared by any of the methods described above utilizing the hyperproducing $LT^+$, $ST^+$ strain as the starting material.

Ent plasmids, containing the gene for LT, ST or both, from stains other than strain 86 can be utilized as the starting material if a drug resistance gene is also present or can be inserted. For example, resistance to tetracycline can be introduced into Ent plasmids by inserting transposon 10 (Tn10) containing a gene for tetracycline resistance into said plasmids. This is done by transduction of *E. coli* K12 containing an Ent plasmid with phage containing Tn10 and selecting for resistance to tetracycline. The resulting plasmid can then be used as starting material in any of the preceding methods.

The LT− CRM+,ST− strain (normal or hyperproducing) produced by any of the methods described above is then mated with an *E. coli* strain which is a recipient in matings and which carries a plasmid with the gene for the colonization factor, K88. This recipient strain is prepared by mating an *E. coli* isolate from a pig, such as strain P104, with a donor strain containing a conjugative plasmid with genes for K88 production and raffinose fermentation (Raf+) (Smith, H. W., and Parsell, Z., *Journal of Gen. Microbiol.*, 87, 129 (1975)). Raf+ transconjugants are selected. The final strains are obtained by selecting for resistance to tetracycline. This results in the isolation of bacteria which are LT− CRM+, ST−, Tc$^R$ and contain the colonization factor K88. Similarly, by mating the LT− CRM+, ST− strains with strains containing a different colonization factor, such as K99 of 987P, strains containing these colonization factors and the LT− CRM+, ST− plasmids are obtained.

The techniques described herein can be utilized for manipulating the genes to form any combination desired. It is possible to make an ST− gene from any ST+ gene by utilizing Tn5 insertions or Ngd mutagenesis. Thus, any plasmid which contains an ST+ gene can be isolated and manipulated as described herein to produce an ST− gene. Similarly, any plasmid which contains an LT+ gene, ST+ gene, or both LT+ and ST+ genes, can be prepared having drug resistance by utilizing a transposon, for example Tn10, as described herein. After the gene for drug resistance has been incorporated into the plasmid, the LT− or ST− genes can be prepared by mutagenesis as previously described. With these techniques it is possible to cross an ST− strain, for example, with an ST+ strain having other desired characteristics, such as a colonization factor or an LT− CRM+ gene, in order to produce an ST− strain having said desired characteristics. By manipulating plasmids normally not occurring in the same cell, it is possible to recombine them in order to provide stains of *E. coli* possessing the desired characteristics. Thus, it is possible to prepare a strain of *E. coli* possessing a plasmid containing an ST− gene and a human colonization factor such as CFA/I, a mobilization plasmid for conjugal transfer of the first plasmid, and may additionally contain, although it need not, a plasmid containing an LT− CRM+(Reis et al, *Inf. and Immun.*, 29, 140 (1980).

The heat labile enterotoxin (LT) consists of two subunits, A and B, with B being mainly responsible for immunogenicity. One can start by isolating a recombinant plasmid containing a mutation in the A subunit. Since this plasmid was not conjugative, a chimeric plasmid can be constructed by ligating a DNA segment containing the mutant LT gene and a gene for chlorampherical resistance to a segment of the F plasmid containing genes for conjugal transfer. This plasmid is readily transmissible to other *E. coli* strains and its B gene is expressed in the new hosts as well as in the original *E. coli* K12 strain.

The new strains of *E. coli* produced by this invention are suitable for use as live vaccines against pathogenic *E. coli*-causing diarrheal diseases. The live vaccines produced by this invention provide protection against pathogenic *E. coli* by (a) producing biologically inactive toxin molecules (LT, ST or both) which can block toxin receptor sites on the intestinal cells; (b) producing an immunologically cross-reactive material which elicits the formation of protective IgA antibodies (as discussed for chlorea in Honda and Finkelstein, (supra); and (c) adhering and growing in the small intestine, hence becoming established and thus blocking growth of pathogenic *E. coli*. The word "vaccine" is used herein in a wide sense, referring to an agent that gives protection not only through eliciting antibodies, but also by other means. The strains of *E. coli* produced by the present invention can be mixed with any sterile, pharmaceutically acceptable diluent. The resultant vaccine is then administered orally to humans or animals, such as calves or piglets, susceptible to pathogenic *E. coli*-caused diarrheal diseases. The strains of *E. coli* administered colonize the small intestine and provide protection as discussed above.

The details of the present invention will be further described by the following examples.

EXAMPLE 1

Preparation of a plasmid containing LT− CRM+ and ST− genes

The Ent plasmid, pCG86, is transferred into *E. coli* K12 as described by Gyles, C. L. et al, *Science*, supra. This plasmid is LT+, ST+, Tc$^R$, Sm$^R$, Su$^R$, Tra+. An ST− mutant is prepared and characterized as described by Silva, M. L. M. etal, supra. This mutant is thus LT+, ST−, Tc$^R$. This mutant is made Tc$^S$ as follows. A single colony LT+, ST−, Tc$^R$ mutant is suspended in 5 ml of minimal medium and incubated with shaking for 6 hours at 32° C. prior to exposure to 15 mg of Ngd/ml for 15 minutes. After centrifugation and washing with minimal medium the bacteria are suspended in 2 ml of minimal medium or neopeptone broth (Dubnau, E. and Maas, W. K., *J. Bacteriol.*, 95, 531 (1968)). These cultures are incubated with shaking for 2 hrs at 37° C.; then penicillin and Tc are added, the former to a concentration of 1000 μg/ml, the latter to 20 μg/ml. Incubation is continued for 16 hrs before 0.1-ml aliquots are plated on neopeptone agar. The plates are incubated at 37° for 1 to 21 days, and colonies appearing on these plates are tested for sensitivity to Tc.

An LT+, ST−, Tc$^S$ mutant is isolated and cultured in neopeptone broth. From an overnight neopeptone culture, 0.1 ml is inoculated into 10 ml of fresh neopeptone broth and incubated with shaking for 3 hrs at 37° C. The bacteria are centrifuged and resuspended in 4.5 ml of Tris-maleic buffer, pH 6.0, containing 200 μg of Ngd per ml. After 30 min of incubation at 37° C. they are centrifuged, washed with g-Syncase medium (Sack, R. B. et al., *J. Infect. Dis.*, 123, 378 (1971), and resuspended in 5 ml of this medium. To 5 ml of fresh g-Syncase medium, 0.5 ml of the mutagenized suspension is added and the culture is incubated with shaking for 16 hrs at 37° C. Then 0.1 ml aliquot is plated on neopeptone agar plates containing 20 g of Tc per ml for the selection of Tc$^R$ mutants. After incubation at 37° C., colonies appearing on these plates are purified.

The colonies are then tested for toxin production. LT is assayed by using the Y1 mouse adrenal tumor cell system of Donta, S. T., et al., supra, as modified for microtiter plates by Sack and Sack, supra as described in Silva et al, supra. LT and ST are also assayed for fluid accumulation in ligated segments of pig intestine as described by Gyles, C. L. and Barnum, D. A., *J. Infect. Dis.* 120, 419 (1969). The colonies which assayed as LT−, ST− are then tested for the production of CRM by a solid phase passive immune hemolysis assay as described by Bramucci and Homes, supra. Colonies which contain a plasmid containing LT− CRM+ and ST− genes are then isolated and cultured. This plasmid also contains the $Tc^R$ gene.

EXAMPLE 2

Preparation of a plasmid containing LT− CRM+ and ST− genes

Plasmid pCG86 in *E. coli* K12 is utilized as the starting material. LT− mutants are prepared and characterized as described in Silva, M. L. M., et al., supra and tested for production of CRM as described by Bramucci and Holmes; supra Colonies which are LT− CRM+, ST+, $Tc^R$ are then isolated and cultured.

Figure 2:
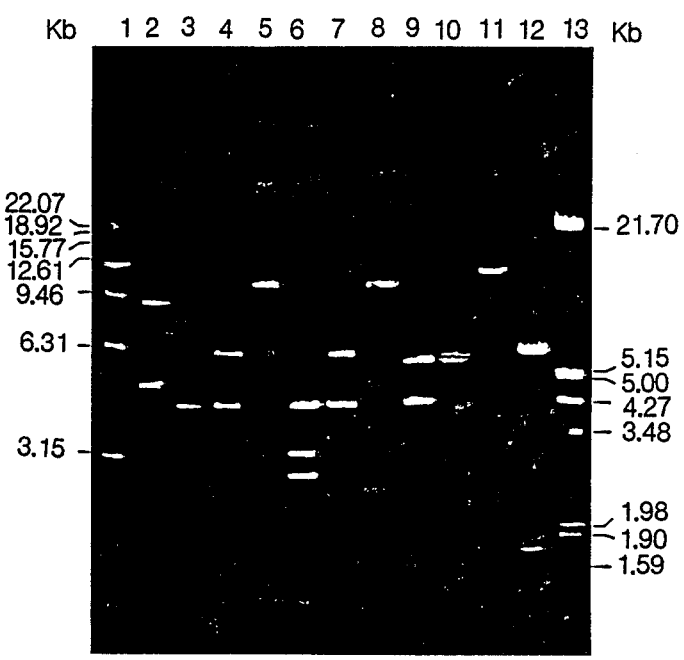
FIG. 2 shows the restriction analysis of pWM2988, pBR322, pPMC2, pPMC21, pPMC4, and pGA22 using 0.75% agarose gel electrophoresis. Lanes 1 through 13 were loaded with the following fragments: (1) Linear oligomers of dv-21 DNA; (2) pWM2988, PvuI; (3) pBR322, PvuI; (4) pPMC2, PvuI; (5) pPMC2, XbaI; (6) pPMC2, PvuI/XbaI; (7) pPMC21, PvuI/XbaI; (8) pPMC21, XhoI; (9) pPMC21, PvuI/XhoI; (10) pPMC4, PvuI/XhoI; (11) pPMC4, XhoI, (12) pGA22, PvuI/XhoI; (13) EcoR1/HindIII. Fragment sizes in kb refer to DNA standards.

Plasmid pCG86 in *E. coli* K12 is cultured in neopeptone broth. This culture is transduced by lambda (λ) phage carrying Tn5 which contains a gene for Kanamycin (Kn) resistance as described by Berg, D. E., in *DNA Insertion Elements, Plasmids and Episomes,* Bukhari, A. I., Shapiro, J. A. and Adhya, S. L., Ed., Cold Spring Harbor Laboratory, Cold Spring Harbor, NY, p 205 (1977) and transduced strains are selected for resistance to Kanamycin. The $Kn^R$ strains are then mated with an F− strain of *E. coli* to eliminate chromosomal insertions of Tn5. A colony which is $Kn^R$ is cultured overnight in a neopeptone broth. 0.1 ml of each strain is added to 0.8 ml of neopeptone broth and incubated for 60 minutes. Tn5 can insert in either the Tc or ST gene and cause insert mutations. By selecting for colonies using tetracycline, colonies are isolated which are $Tc^R$ and some are ST−, $Kn^R$ and LT+. These colonies are verified to be ST−, by performing the assays described by Gyles, C. L. and Barnum, D. A., supra. These bacteria are grown and infected with P1 phage and P1 phage isolated from the lysate as described by Pfister, A., et al, supra.

The LT− CRM+, ST+, $Tc^R$ plasmid is transferred to a bacterial strain which is $Kn^S$ by mating as described above. Bacteria are isolated which are $Tc^R$ and thus also carry the LT− CRM+, ST+ plasmid. The resulting bacteria are then transduced with the P1 phage containing the LT+, ST−, $Kn^R$ plasmid prepared above as described by Pfister, A., et al., supra. Colonies are selected from $Kn^R$ and examined for LT− and ST− as described by Silva, M. L. M., et al, supra. The LT− CRM+, ST− strains are isolated and cultured. These strains contain plasmids which are LT− CRM+ and ST− as well as $Kn^R$.

EXAMPLE 3

Preparation of a plasmid for hyperproducing LT

A plasmid for hyperproducing LT is prepared by inserting Tn3 containing a gene for ampicillin (Ap) resistance into a plasmid containing an LT gene. The plasmid, Rscl3, is the source of Tn3. A strain of *E. coli* carrying Rscl3 is mated with *E. coli* K12 carrying pCG86 by following the procedure described by Goebel, et al, supra. Colonies containing plasmids pCG86 and Rsc13 are selected for resistance to Ap and Sm. Colonies which are $Ap^R$ and $Sm^R$ are then mated with an F− strain of *E. coli* as described by Goebel et al., supra. Colonies are selected for resistance to Ap and Sm. Colonies which are $Ap^R$ and $Sm^R$ are then assayed for LT as described in Example 1 and compared to *E. coli* K12 containing pCG86 as the control. The colonies which produce more LT than the control are identified as hyperproducing LT. These colonies contain a plasmid which contains a hyperproducing LT+ gene.

Plasmids which contain a hyperproducing LT− CRM+ gene and an ST− gene are prepared as described in Examples 1 or 2.

EXAMPLE 4

Preparation of a strain which is LT− CRM+, ST−, K88+

A strain containing any one of the plasmids prepared above and also containing a colonization factor is prepared as follows. A bacterial strain which is a recipient in matings and contains a plasmid having the gene coding for colonization factor K88 (i.e., it is K88+), is mated with the LT− CRM+, ST−, $Tc^R$ strain produced in Examples 1 to 3, by following the mating procedure described in Example 2. A transconjugant is selected for resistance to tetracycline. This strain contains a plasmid having the LT− CRM+ and ST− genes and a different plasmid having the K88+ gene.

EXAMPLE 5

Preparation of plasmid containing eltA−, eltB+ genes by recombinant DNA technology The plasmid pWM2988 is constructed by cloning an 8.9 kb BamHI fragment of pCG86 into the BamHI site of pBR313 as described by Picken, R. N. et al *Infect. Immun* 42, 269 (1983). This plasmid is $Amp^R$ LT+ (elt), STII (estA)+. The genes carried on a 5.9 kb Pvu I fragment were subcloned with the PvuI site of pBR322 to form a plasmid pPMC2. Plasmid pPMC2 is LT (elt)+, STII (estA)− $Tet^R$ $AMP^R$. The nucleotide sequences of eltA and eltB showed a single XBaI recognition site near the NH2 terminus of eltA.

Plasmid pPMC2 was cleaved at the XbaI site. The single-stranded ends were filled in with the Klenow fragment of DNA polymerase I and blunt end ligated to yield covalently closed plasmid DNA. The XbaI site is converted to 5'-TCTAGCTAGA-3', generating a stop codon 5 codons downstream from the XbaI site. A mutation at this XbaI site results in an EltA−B+ plasmid that produces biologically inactive, antigenically active LT.

*E. coli* C 600 was transformed to tetracycline resistance after in vitro mutagenesis of pPMC2. A plasmid, pPMC21, was selected from one of the colonies that was negative in the Y-1 adrenal cell assay and positive in the PIH assay. The elt genes were subcloned from pPMC21 into the vector pGA22 according to the method of An et al (*J. Bacteriol.* 140, 400 (1979)). Plasmid pPMC21, which has a single XhoI site (lane 8, FIG. 2) was doubly digested with PvuI and XhoI. The larger 5.6 kb PvuI/XhoI fragment (1 and 9, FIG. 2) was isolated from an agarose gel and purified. Similarly, pGA22, which also has a single XhoI site, was doubly digested with PvuI and XhoI. The larger 5.8 kb PvuI/XhoI fragment (lane 12, FIG. 2) was isolated from an agarose gel, purified and ligated to the 5.6 kb fragment of pPMC21. The resultant 11.4 kb plasmid transformed C600 to chloramphenicol and tetracycline resistance and was designated pPMC4. (FIG. 1). The single XhoI site was verified (lane 11, FIG. 2) and a PvuI/XhoI digest of pPMC4 showed 2 bands of fragments of the expected sizes, 5.6 kb and 5.8 kb (lane 10, FIG. 2). As expected, the Y-1 assay and the pig intestinal loop assay were negative and the PIH assay was positive for cells carrying this plasmid.

Construction of a transferable LTA−B+ plasmid

Figure 3:
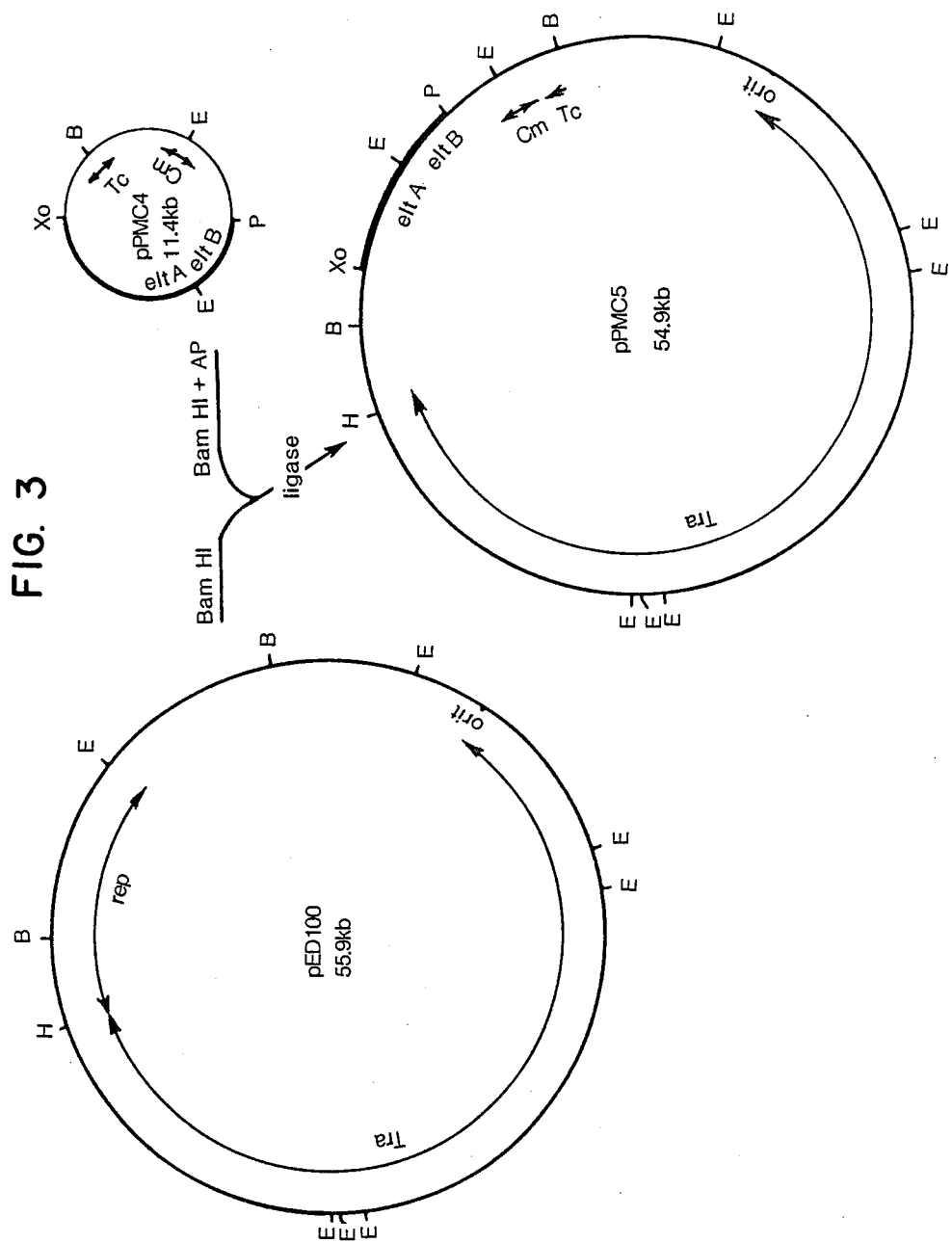
FIG. 3 illustrates the construction of plasmid pPMC5, wherein the following abbreviations apply: B, BamHI; E, EcoRI; H, HindIII, P, PvuI; Xo, XhoI; Cm, Tc, Resistance to chloramphenicol and tetracycline; elt, heat-labile enterotoxin; rep, replication region; oriT, origin of transfer; tra, transfer genes; AP, alkaline phosphatase.
Figure 4:
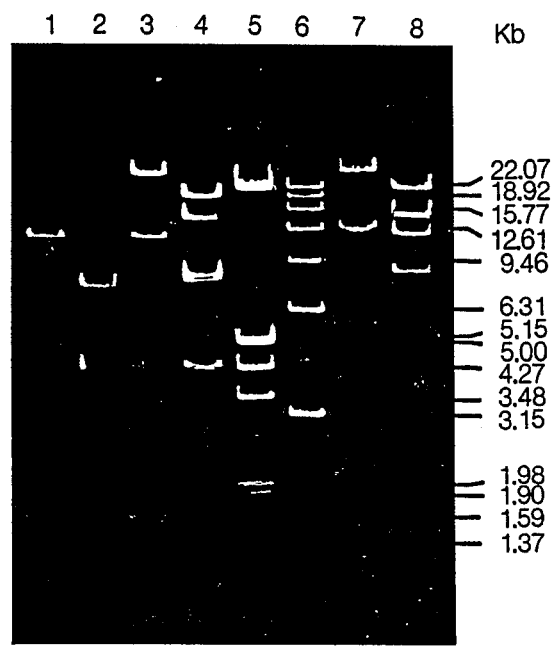
FIG. 4 shows the restriction analysis of pPMC4, pPMC5, and pED100 using 0.75% agarose gel electrophoresis. Lanes 1 through 8 were loaded with the following fragments: (1) pPMC4, BamHI (2) pPMC4, EcoRI (3) pPMC5, BamHI (4) pPMC5, EcoRI (5) ,EcoRI and HindIII (6) Linear oligomers of dv-21 DNA (7) pED100, BamHI (8) pED100, EcoRI. Fragment sizes in kb refer to DNA standards.

The entire replication and transfer genes of F are in a 55.9 kb plasmid, pED100 (Willets and Johnson, Mol. Gen. Genet., 182, 520 (1981)) that has a single Hind III site and 2 BamHI sites that are in regions outside the tra genes. Cloning of these transfer genes into pPMC4 would provide a conjugally transferable multicopy LTA−B+ chloramphenicol resistant plasmid. The construction of such a plasmid is shown in FIG. 3. Plasmid pED100 was cleaved with BamHI to yield two fragments of approximately 43.5 kb and 12.4 kb (lane 7, FIG. 4). This digest was then mixed and ligated with BamHI-linearized pPMC4 DNA, treated with calf intestinal phosphatase (CIP) to prevent ligation of the vector. The ligated mixture was used to transform E. coli C600. Since the tra gene fragment has no selectable marker and the BamHI site in pPMC4 is located in the gene for tetracycline resistance, recombinants should be tetracycline sensitive and chloramphenicol resistant; transformed cells sensitive to tetracycline could be enriched by penicillin treatment. Accordingly the transformation mixture was treated with penicillin. The cultures were shaken at 37° C. for 1 hour and penicillin was added to a final concentration of 1000 units per ml. After shaking for 30 min., cells were collected and allowed to grow overnight in Tryptone yeast extract (TYE) medium. For selecting transferable recombinants, mating was performed with the transformed cells as donors and chloramphenicol sensitive cells of strain KL 320 as recipients and chloramphenicol resistant colonies were selected. Ten transconjugant colonies were obtained. Six of the ten transconjugants screened on agarose gels for the presence of plasmids by the method of Kado and Liu (J. Bacteriol., 45, 1365 (1981)) showed the presence of a large plasmid migrating with the same mobility as pED100, and four had a larger plasmid. All ten were negative in the Y-1 cell assay and in the pig intestinal loop assay, positive in the PIH assay, and showed high transfer frequencies of the plasmid in matings. One of the six isolates was selected for further study and its plasmid was designated pPMC5. A BamHI digest of this 54.9 kb plasmid yielded two DNA fragments of 11.4 kb and 43.5 kb The orientation of these fragments in pPMC5 as shown in FIG. 3 was determined by consideration of the DNA fragment sizes produced by EcoRI digests of pPMC4 (lane 2, FIG. 4), pPMC5 DNA (lane 4, FIG. 4) and pED100 (lane 8, FIG. 4).

Construction of potential vaccine strains.

Strain C600 (pPMC5) was mated with 11 non-enterotoxigenic porcine strains, obtained from C. Gyles, that were surmised to colonize the small intestine (Table 1).

TABLE 1

| Description of Prototrophic Porcine Strains | | |
|---|---|---|
| Strains | Serotype | Relevant Phenotype[a] |
| G58 | 0101:K28 | Tc[r] |
| G58-1[b] | 0101:K28 | Tc[s] |
| G58-6[b] | 0101:K28 | Tc[s] |
| W2954' | 0101:K30 | Tc[r]Sp[r] |
| W2954-1[c] | 0101:K30 | Sp[r]Tc[s] |
| 0919W | 0101:K30 | Tc[r]Km[r] |

TABLE 1-continued

| Description of Prototrophic Porcine Strains | | |
|---|---|---|
| Strains | Serotype | Relevant Phenotype[a] |
| 0919F | 0101:K30 | Tc[r]Km[r] |
| G59 | 0101:K30 | Tc[r]Km[r] |
| 672 | 0138:K81 | Tc[r]Km[r] |
| 568 | 0138:K81 | Ap[r]Tc[r] |
| G24 | 09:K103 | Tc[r] |

[a]Ap, ampicillin; Km, kanamycin; Sp, spectinomycin; Tc, tetracycline, [r], drug resistant; [s], drug sensitive
[b]Tetracycline sensitive derivatives of strain G58.
[c]Tetracycline sensitive derivative of strain W2954.

These strains belong to serotypes that are usually enterotoxigenic. They were isolated from piglets with diarrhea and in feeding experiments with piglets were found to be excreted for at least 3 days. Transfer of pPMC5 with selection for chloramphenicol resistance occurred with high frequency (about one percent of the donor imput) with 9 recipients. One transconjugant from each successful mating was examined for plasmid DNA and showed the presence of a plasmid considered to be pPMC5, since it had the expected size and it was not seen in the recipient controls. The 9 transconjugants were negative in the Y-1 assay and positive in the PIH test, with titers ranging from 4 to 32 times that obtained with strains carrying the parental plasmid pCG86 (Table 2).

TABLE 2

| Y-1 cell Assay and PIH Test of Strains Containing Mutant LT Plasmids | | |
|---|---|---|
| Strains | Y-1 cell assay | Titer in PIH test[a] |
| G58 (pPMC5) | − | 32 |
| G58-1 (pPMC5) | − | 32 |
| G-586 (pPMC5) | − | 32 |
| W2954 (pPMC5) | − | 8 |
| 0919W (pPMC5) | − | 8 |
| 0919F (pPMC5) | − | 8 |
| 6721 (pPMC5) | − | 16 |
| 5686 (pPMC5) | − | 1 |
| G59 (pPMC5) | − | 4 |
| Control strains: | | |
| C600F (pPMC5) | | 8 |
| 289-1 | + | 1 |

[a]Relative to titer of strain 289-1, which carries plasmid pCG86.

Earlier we had tried to introduce the mutant plasmid pPMC4 (FIG. 1) into the 11 porcine isolates by transformation, but obtained transformants only with strain G58 and two tetracycline-sensitive derivatives, G58-1 and G58-6, isolated from it by the method of Bochner et al. (J. Bacteriol., 143, 926 (1980)). Subsequently we attempted transfer of pPMC4 by mobilization with the conjugative plasmid R538 (Santos et al, J. Bacteriol. 124, 1240–1247 (1975)). A donor strain, C600 (pPMC4, R538) was mated with two tetracycline-sensitive derivatives, G58-1 and W295-1 and tetracycline resistant transconjugants were selected. These were obtained with a moderate (about 0.1% of donor input) frequency and 20 transconjugants from each mating were examined for plasmid DNA. They showed patterns of bands suggesting that recombinations had occurred among the plasmids. Arrangement of the patterns into discrete types was difficult to achieve. All 20 transconjugants from the mating with G58-1 were positive in the PIH test, and only 3 of the transconjugants from the mating with W2954-1 were positive. The titers of the positive strains ranged from 4 to 64 times that of a PCG86-carrying strain. In contrast, the pPMC4 transformants had the expected plasmid profile and had titers that were uniformly 32 times that of a pCG86-carrying strain.

From these results it is clear that direct transfer of a conjugative plasmid carrying a mutant toxin gene is the most advantageous method for the construction of potential vaccines.

Stability of pPMC4 and pPMC5 in various hosts

An effective live oral vaccine should be stable. Therefore this property was determined for the strains G58, G58-1 and G58-6 harboring the plasmids pPMC4 and pPMC5. After approximately 20 generations in drug free medium following subculture from medium containing chloramphinicol, the loss of chloramphenicol resistant cells from populations of the 6 strains was determined and the results are presented in Table 3. The data indicate that pPMC5 is stably maintained in the three strains. Although the loss of pPMC4 was greater after 20 generations than that of pPMC5, the loss of this plasmid per generation is considered to be small.

TABLE 3

Plasmid loss After Growth in Drug-Free Medium

| Strains | Loss of plasmid after 20 generations (% of population) |
|---|---|
| G58 | 2.9 |
| G58-1 (pPMC4) | 8.9 |
| G58-6 (pPMC4) | 27.6 |
| G58 (pPMC5) | 0.21 |
| G58-1 (pPMC5) | 0.42 |
| G58-6 (pPMC5) | 0.27 |

While the invention has been described in connection with specific embodiments thereof, it will be understood that it is capable of further modifications and can be utilized to prepare mutant toxin strains from other animal sources for veterinary or clinical purposes. This application is intended to cover any variations, uses or adaptions of the invention following, in general, the principles of the invention and including such departures from the present disclosure as come within known and customary practice within the art to which the invention pertains.

What is claimed is:

1. A plasmid which comprises a gene coding for an immunologically active, conjugably transferable, non-toxin, heat-labile *Escherichia Coli* enterotoxin and a gene coding for a non-toxic, heat-stable *Escherichia Coli* enterotoxin.

2. The plasmid of claim 1, further comprising transposon 3.

3. A strain of *Escherichia coli* comprising the plasmid of claim 1.

4. A strain of *Escherichia coli* comprising the plasmid of claim 2.

5. The *Escherichia coli* of claim 3, further comprising a K88 colonization factor.

6. The *Escherichia coli* of claim 4, further comprising a K99 colonization factor.

7. The *Escherichia coli* of claim 5, wherein said *Escherichia coli* is compatible with humans or animals.

8. The *Escherichia coli* of claim 6, wherein said *Escherichia coli* is compatible with humans or animals.

9. The *Escherichia coli* of claim 5, wherein said microorganism *Escherichia coli* is compatible with hogs.

10. The *Escherichia coli* of claim 6 wherein said microorganism *Escherichia coli* is compatible with hogs.

11. A live vaccine comprising the *Escherichia coli* of claim 5 and a sterile, pharmaceutically acceptable carrier.

12. A live vaccine comprising the *Escherichia coli* of claim 6 and a sterile, pharmaceutically acceptable carrier.

13. A live vaccine comprising the *Escherichia coli* of claim 3 and a sterile, pharmaceutically acceptable carrier.

14. A live vaccine comprising the *Escherichia coli* of claim 4 and a sterile, pharmaceutically acceptable carrier.

15. A method of vaccinating hogs which comprises orally administering the live vaccine of claim 11.

16. A method of vaccinating hogs, cattle, and sheep which comprises orally administering the live vaccine of claim 12.

17. A method of vaccinating hogs which comprises orally administering an effective amount of a live vaccine comprising the *Escherichia coli* of claim 9 and a sterile, pharmaceutically acceptable carrier.

18. A method of vaccinating hogs which comprises orally administering an effective amount of a live vaccine comprising the *Escherichia coli* of claim 10 and a sterile, pharmaceutically acceptable carrier.

19. A method for preparing the plasmid of claim 1, which comprises mutating a plasmid containing a gene coding for an heat-liable enterotoxin and a gene coding for a non-toxic, heat-stable enterotoxin and isolating a resulting plasmid comprising a gene coding for an immunologically active, non-toxic, heat-labile enterotoxin and a gene coding for a non-toxic, heat-stable enterotoxin.

20. A method for preparing the plasmid of claim 1, which comprises transducing a first plasmid comprising a gene coding for an immunologically active, non-toxic, heat-labile enterotoxin and a gene coding for a heat-stable enterotoxin by a second plasmid comprising a gene coding for a heat-labile enterotoxin and a gene coding for a non-toxic, heat-stable enterotoxin, and isolating a resulting plasmid comprising a gene coding for an immunologically active, non-toxic, heat-labile enterotoxin and a gene coding for a non-toxic, heat-stable enterotoxin.

21. A method for preparing the plasmid of claim 2, which comprises mutating a plasmid containing a gene coding for a heat-labile enterotoxin, a gene coding for a non-toxic, heat-stable enterotoxin and transposon 3 and isolating a resulting plasmid comprising a gene coding for an immunologically active, non-toxic, heat-labile enterotoxin, a gene coding for a non-toxic, heat-stable enterotoxin and transposon 3.

22. A method for preparing the plasmid of claim 2, which comprises transducing a first plasmid comprising a gene coding for an immunologically active, non-toxic, heat-labile enterotoxin, a gene coding for a heat-stable enterotoxin and transposon 3 by a second plasmid comprising a gene coding for a heat-labile enterotoxin and a gene coding for a non-toxic, heat-stable enterotoxin and isolating a resulting plasmid comprising a gene coding for an immunologically active, non-toxic, heat-labile enterotoxin, a gene coding for a non-toxic, heat-stable enterotoxin and transposon 3.

23. A method for preparing the *Escherichia coli* of claim 5, which comprises mating a microorganism having a plasmid containing a gene coding for an immunologically active, non-toxic, heat-labile enterotoxin and a gene coding for a non-toxic, heat-stable enterotoxin with a microorganism having a colonization factor, and isolating a resulting microorganism having said plasmid and said colonization factor.

24. A method for preparing the *Escherichia coli* of claim 6, which comprises mating a microorganism having a plasmid comprising a gene coding for an immunologically active, non-toxic, heat-labile enterotoxin, a gene coding for a non-toxic heat-stable enterotoxin and transposon 3 with a microorganism having a colonization factor and isolating a resulting microorganism having said plasmid and said colonization factor.

* * * * *